United States Patent
Schulz et al.

(10) Patent No.: US 8,038,677 B2
(45) Date of Patent: Oct. 18, 2011

(54) SURGICAL INSTRUMENT

(75) Inventors: Peter Schulz, Loeffingen (DE); Dieter Weisshaupt, Immendingen (DE); Markus Nesper, Tuttlingen (DE); Konstantin Faulhaber, Frittlingen (DE); Theodor Lutze, Balgheim (DE)

(73) Assignee: Aesculap AG, Tuttlingen (DE)

( * ) Notice: Subject to any disclaimer, the term of this patent is extended or adjusted under 35 U.S.C. 154(b) by 1258 days.

(21) Appl. No.: 11/716,523

(22) Filed: Mar. 8, 2007

(65) Prior Publication Data

US 2007/0213769 A1     Sep. 13, 2007

Related U.S. Application Data

(63) Continuation of application No. PCT/EP2005/010501, filed on Sep. 28, 2005.

(30) Foreign Application Priority Data

Oct. 1, 2004   (DE) .......................... 10 2004 049 247

(51) Int. Cl.
*A61B 17/32* (2006.01)
(52) U.S. Cl. ......................................... 606/79
(58) Field of Classification Search .................... 606/79, 606/83, 84, 184, 185
See application file for complete search history.

(56) References Cited

U.S. PATENT DOCUMENTS

| | | | |
|---|---|---|---|
| 2,625,682 A | 1/1953 | Cristiano | |
| 3,752,161 A | 8/1973 | Bent | |
| 3,815,604 A | 6/1974 | O'Malley et al. | |
| 3,884,238 A | 5/1975 | O'Malley et al. | |
| 3,913,585 A | 10/1975 | Wolvek | |
| 4,590,935 A | 5/1986 | Ranalli | |
| 4,848,338 A | 7/1989 | De Satnick et al. | |
| 4,943,294 A | 7/1990 | Knapp | |
| 5,042,362 A * | 8/1991 | Schulze | 91/29 |
| 5,163,598 A | 11/1992 | Peters et al. | |
| 5,339,723 A | 8/1994 | Huitema | |
| 5,361,583 A | 11/1994 | Huitema | |
| 5,451,227 A | 9/1995 | Michaelson | |
| 5,569,258 A | 10/1996 | Gambale | |
| 6,273,898 B1 | 8/2001 | Kienzle et al. | |
| 6,599,291 B1 | 7/2003 | Foley et al. | |
| 2004/0122433 A1 | 6/2004 | Loubens et al. | |

FOREIGN PATENT DOCUMENTS

| | | |
|---|---|---|
| EP | 1 362 556 | 11/2003 |
| EP | 0 716 578 | 5/2004 |
| EP | 1 419 741 | 5/2004 |
| WO | 2004/086988 | 10/2004 |

\* cited by examiner

*Primary Examiner* — Nicholas Woodall
(74) *Attorney, Agent, or Firm* — Lipsitz & McAllister, LLC

(57) ABSTRACT

The invention relates to a surgical instrument comprising a handling part and a tool part that encompasses at least one movably mounted tool which is actuated via a force-transmitting and/or actuating mechanism. Said force-transmitting and/or actuating mechanism is operated from the handling part and is provided with a fluid-operated drive unit. In order to improve said surgical instrument such that the same can be operated with as much sensitivity as possible, the movably mounted tool can be impinged upon a first actuation force in a first driven position while being impinged upon by at least one second actuation force in a least one second driven position with the aid of the drive unit.

34 Claims, 7 Drawing Sheets

SURGICAL INSTRUMENT

This application is a continuation of international application number PCT/EP2005/010501 filed on Sep. 28, 2005.

The present disclosure relates to the subject matter disclosed in international application number PCT/EP2005/010501 of Sep. 28, 2005 and German application number 10 2004 049 247.6 of Oct. 1, 2004, which are incorporated herein by reference in their entirety and for all purposes.

BACKGROUND OF THE INVENTION

The present invention relates to a surgical instrument comprising a handling part and a tool part, wherein the tool part comprises at least one movably mounted tool, which is actuable by means of a force-transmitting and/or actuating mechanism that is operable from the handling part, and that the force-transmitting and/or actuating mechanism comprises a fluid-operable drive unit.

Surgical instruments of the initially described type are known for example in the form of bone punches for the removal of bone, cartilage or similar tissue. The drawback of the known bone punches is that sensitive actuation of the movably mounted tool by means of the fluid-operable drive unit is either possible only to a limited extent or even totally impossible. The reason for this is that the drive unit can either be loaded with a fluid flow of specific pressure or not. This however has the disadvantageous consequence that, in the event of actuation of the actuating mechanism, the instrument is generally transferred abruptly from an inoperative or basic position into a working position or vice versa. This may lead for example to a bone punch removing, not a desired tissue area, but a tissue area lying adjacent thereto.

Therefore, it would be desirable to provide a surgical instrument of the initially described type which may be operated as sensitively as possible.

SUMMARY OF THE INVENTION

In a surgical instrument of the initially described type, according to the invention it is provided that with the drive unit in a first driving position the movably mounted tool can be subjected to a first actuating force and in at least a second driving position can be subjected to at least a second actuating force.

The development according to the invention of known surgical instruments has the advantage of allowing a surgeon to control the instrument more sensitively while in use. Particularly when the first actuating force differs from the second actuating force, it is possible for example for the tool in the first drive position to be subjected to a force that, for example in the case of a bone punch, is insufficient to cut through tissue but at most sufficient to move the tool up to the tissue. This allows the surgeon to position the instrument in a desired manner and only then transfer the instrument into the second drive position, in which the tool occupies a working position, in which it is therefore able to cut tissue for example.

It is advantageous when with the drive unit in a third driving position the movably mounted tool is subjected to a third actuating force. This allows the surgeon to control the instrument even more sensitively as he may exert for example three different actuating forces on the movably mounted tool by means of the force-transmitting and/or actuating mechanism.

Preferably, the third actuating force corresponds to the sum of the first and second actuating force. This allows the drive unit to be designed for example with two fluid piston units, which may each adopt two drive positions. This leads to a marked simplification of in particular the construction of the drive unit.

In an advantageous manner, a ratio of the first and second actuating force lies in the range of 4:1 to 9:1. This allows a force of approximately 10 to 20% of the maximum force available from the drive unit to be transmitted to the movable tool in the first drive position. In the case of a bone punch, for example, this force is then insufficient to cut off tissue that is to be removed.

The construction of the instrument is further simplified when the drive unit comprises a linear drive. This might be disposed parallel to the longitudinal direction but is preferably disposed inclined relative to the longitudinal direction. In this way, it may be disposed inside a handle of the handling part. The instrument may therefore be constructed in a particularly compact, handy manner, for example with a handling part in the form of a pistol grip.

To make it possible to dispense entirely with an electrical energy supply, it is advantageous if the linear drive comprises at least one fluid cylinder. Fluid cylinders are particularly low-maintenance and generally have a long service life.

In order to construct the linear drive entirely on the basis of fluid cylinders, it is advantageous if the linear drive comprises two coupled, separately controllable fluid cylinders. This allows the one fluid cylinder to be loaded independently of the other fluid cylinder with a fluid for generating a driving force. Equally, however, both fluid cylinders may also be loaded simultaneously with a fluid, with the result that altogether three active drive positions are selectable. If neither of the two fluid cylinders is loaded with a fluid for generating a driving force, the instrument occupies an inoperative position. This position is subsequently not described as a drive position.

In order to be able to select three different actuating forces, it is advantageous if the two fluid cylinders have different effective cross sections. If their effective cross sections are identical, then either none, half, or all of the driving force available from the drive unit may be generated. If however the effective cross sections are different, then a first driving force may be less than 50% of the maximum force. The second driving force then corresponds to the difference between the first driving force and the maximum force and is therefore greater than half of the maximum force.

Drive positions with in particular 10 to 20% of the maximum force, 80 to 90% of the maximum force and the maximum force may be selected when a ratio of the effective cross sections lies in a range of 4:1 to 9:1.

In an advantageous manner, the at least one fluid cylinder is a pneumatic and/or hydraulic cylinder. A pneumatic cylinder may be operated for example with compressed air, such as is usually available in every operating theatre. This has the added advantage that even a not completely sealed system is in principle still operational. Since moreover only air may escape from the system, this does not lead to any compromising of a patient. This might however be the case if hydraulic cylinders were used with a physically non-compatible fluid and a leakage of the drive system were to occur.

According to a preferred form of construction of the invention, it may be provided that the at least one fluid cylinder is a double-acting fluid cylinder. This allows a piston of the at least one fluid cylinder to be loaded from one side with a fluid for generating a desired driving force. In the opposite direction the piston may equally be loaded with a fluid in order to move the instrument back into a basic position and/or keep it in the basic position. The basic position in an instrument may be selected for example in such a way that the movably mounted tool occupies an open position, i.e. by subjecting it to an actuating force it is transferred from the basic position into a working position, in which it performs a function, for example cuts or holds tissue.

In order to operate the instrument as a bone punch, it is advantageous when the instrument is designed for the removal of bone, cartilage or similar tissue, having a shank, which extends in a longitudinal direction and carries on its distal end a cutting plate, which is disposed transversely of the longitudinal direction or inclined relative to this longitudinal direction, if the movably mounted tool is a cutting element mounted displaceably on the shank and carrying on its distal end a cutting edge, which is directed towards the cutting plate and movable towards the cutting plate for the cutting of tissue.

It is particularly advantageous if the tool part is detachably connectable to the handling part. This is particularly easy to achieve when there is disposed on the proximal end of the shank a first coupling element for detachable, positive connection to the force-transmitting and/or actuating unit, which has a second coupling element corresponding to the coupling element, and if the first coupling element is a polygon, the outer faces of which are directed radially outwards from a longitudinal axis of the shank. A polygon is particularly easy to manufacture and moreover allows the handling part to be disposed on the tool part in a plurality of discrete rotational positions around the longitudinal axis of the shank. In this case, the number of possible rotational positions usually corresponds to the number of outer faces of the polygon.

Four, six or eight defined rotational positions are selectable when the polygon is a quadrilateral, a hexagon or an octagon. What is more, the design as a polygon is suitable for ensuring that only tool parts that are approved for the handling part may be connected to the handling part. The coupling element therefore simultaneously forms a kind of coding element for coding a specific type of tool part.

It is advantageous if the shank at its proximal end is shaped like a sleeve and if the cutting element penetrates the sleeve-like end of the shank. This makes the construction of the shank particularly simple. Furthermore, the sleeve-like end of the shank forms a guide in longitudinal direction for the cutting element.

In order that the cutting element may be connected easily to the force-transmitting and/or actuating mechanism, it is advantageous if it carries-on its proximal end a third coupling element, which is detachably connectable to a drive element of the force-transmitting and/or actuating mechanism, and if the third coupling element is adjoined by stops acting in longitudinal direction of the shank. For example, the drive element may engage between the stops acting in longitudinal direction of the shank or, if the third coupling element is designed in the form of a projection, engage around the lateral stops on the coupling element or even around the coupling element. In this way, a reliable connection and transmission of the driving force from the force-transmitting and/or actuating mechanism to the cutting element may be achieved.

It is advantageous if, in an inoperative position of the instrument, in which no actuating force is exerted by the force-transmitting and/or actuating mechanism in an actuating direction on the tool, a retaining force may be exerted on the tool by the force-transmitting and/or actuating mechanism in a retaining direction opposite to the actuating direction. Without actuation of the force-transmitting and/or actuating mechanism it is therefore ensured that the instrument always occupies the inoperative position. It is therefore situated always in a defined basic position prior to surgical use. By virtue of the exerted retaining force, moreover, unintentional handling, i.e. holding of the instrument in such a way that the movably mounted tool is oriented parallel to the direction of gravitational force, does not lead to movement of the instrument under the action of gravitational force.

It is advantageous if the force-transmitting and/or actuating mechanism comprises an actuating member for actuating the drive unit, if the actuating member is movable from a non-actuated basic position, in which the instrument occupies the inoperative position, into an activation position, in which the drive unit occupies the first drive position, and into at least a second activation position, in which the drive unit occupies the second drive position. This allows a surgeon to operate the instrument in a desired manner, namely, to transfer the actuating member from the non-actuated basic position into a first activation position in order to subject the movably mounted tool for example to a low driving force. He may however also actuate the actuating member in such a way that the movably mounted tool is subjected to a maximum force. The actuating member may, but need not necessarily, be of a one-piece construction. It would be conceivable in particular to divide the actuating member, for example in order to control two fluid cylinders separately, for example by means of two independent control valves which a surgeon may, in a similar manner to a trumpet player, actuate independently of one another.

In order to indicate to the surgeon the position, in which the instrument is situated, it is advantageous if the actuating member is held under spring bias in the basic position. A surgeon therefore always knows, when he picks up the instrument, that it is not actuated.

A particularly simple construction of the instrument is achieved if the actuating member is mounted pivotably. In particular, a mounting about a pivotal axis parallel to or transversely of the longitudinal direction of the instrument may be provided.

According to a further, preferred form of construction of the invention, it may be provided that in the first activation position a first resetting force acts upon the actuating member, that in the second activation position a second resetting force acts, and that the second resetting force is greater than the first resetting force. In this way, the surgeon receives tactile feedback about the actuating position or activation position of the actuating member. If, for example, the driving force in the first drive position is lower than the driving force in the second drive position, this is indirectly communicated to the surgeon by the actuating member. Without having to look at a scale, a surgeon may sense the drive position and hence which driving force is being exerted on the movably mounted tool.

In order to allow a clear distinction between the two activation positions, it is advantageous if the second resetting force is at least twice as great as the first resetting force.

Resetting forces are particularly easy to generate if, for generating the first and second resetting force, there is provided a resetting unit comprising a first elastic resetting member and a second elastic resetting member. A desired resetting force may therefore be associated with each drive position by selecting a specific elastic resetting member.

The first and/or the second resetting member is advantageously a spring element. A reliable resetting member may be provided for example in the form of a helical spring.

It may further be advantageous if the resetting unit is designed to act directly or indirectly upon a control member for controlling the drive unit or upon the actuating member. This further simplifies the construction of the instrument, thereby allowing a particularly compact construction.

According to a preferred form of construction of the invention, a control member may be provided for controlling the drive unit and that the actuating member acts directly or indirectly upon the control member. Such a development is advantageous particularly when an actuating circuit and a working circuit are not operated with the same form of energy. For example, one circuit may be operated electrically, another by means of a pressure-loaded operating means, for example a fluid. This entails a conversion of control signals, for example electrical or mechanical, into specific fluid flows or electrical signals for the drive unit.

The construction of the instrument becomes particularly simple if the control member comprises at least one control valve. The control valve may be actuable for example electrically, electronically or mechanically. This makes it possible to provide a mechanical, electrical or electronic actuating member.

In order to be able to realize three different drive positions, it is advantageous if the at least one control valve has at least three different switching positions. This makes it possible for example to realize an inoperative position of the instrument as well as a first and a second drive position, in which a first and a second actuating force may be exerted on the movably mounted tool.

It is advantageous if the control valve comprises a valve plunger, when on the valve body a least one port connectable to a fluid source and two ports for each double-acting fluid cylinder are provided, when in a first position of the valve plunger at least one of the fluid cylinders can be loaded with fluid in a retaining direction, when in a second position of the valve plunger at least one of the fluid cylinders can be loaded at both sides with different fluid flows, and when in a third position of the valve plunger at least one of the fluid cylinders can be loaded with a fluid counter to the retaining direction. By virtue of the loading at both sides of at least one of the fluid cylinders in the second position of the valve plunger a particularly gentle transfer from the first into the second and then also into the third position of the valve plunger may be realized. In particular, it is possible with such a control valve to subject one or more of the double-acting cylinders to a retaining force, in a second position to load one of the fluid cylinders with a fluid flow counter to the retaining direction in order to generate a first, low actuating force, and finally in the third valve position to load some or all of the fluid cylinders with a fluid in order to generate a maximum driving force.

In order as far as possible to generate three different driving forces with the drive unit, it is advantageous if in the second position of the valve plunger a fluid flow is distributed unevenly to the two ports of at least one fluid cylinder. By this means, the at least one fluid cylinder is moved in a defined manner by a specific force difference in a predetermined direction and so either a retaining force or a driving force is generated.

It is advantageous if the valve plunger is provided with a plurality of annular grooves and in a valve body in different switching positions defines different annular chambers, the ratios of cross section of which in dependence upon a fluid pressure are mutually adapted in such a manner that in the second switching position only a fraction of a maximum actuating force may be generated by the at least one fluid cylinder. In principle, it would be conceivable with one control valve to operate only a single fluid cylinder, wherein in different switching positions of the control valve a double-acting fluid cylinder is loaded with different pressure differences at both sides of its piston in order thereby to generate different driving forces. The valve plunger of the described design is easy to manufacture. Furthermore, this allows easy selection of desired driving force ratios.

In an advantageous manner, at least two control valves are provided, each having at least two switching positions. In this way, a total of four switching positions, including an inoperative position, may be defined. Two control valves have the advantage that either none, one of the two or both simultaneously may be pressed. A surgeon can therefore also immediately know; in which drive position the instrument is situated.

In an advantageous manner, the at least two control valves are manually separately actuable. A surgeon can therefore tell directly by touch or feel, in which working position the instrument is situated.

It is advantageous if on the tool part at least one coding unit is provided for coding the nature and/or type of the tool part and when on the handling part a decoding unit is provided for decoding the nature and/or type of the tool part. By means of a coding of the tool part, the handling part may for example be set so as to limit a maximum force that may be generated by the drive unit. Particularly when sensitive tool parts are used, this may prevent damage to the tool part. The coding moreover makes only approved tool parts being connectable to the instrument.

According to a preferred form of construction of the invention, it may be provided that the at least one coding unit comprises no or at least one projection protruding from the tool part or at least one recess disposed in the tool part, that the decoding unit comprises an operating-mode switching member that corresponds to the at least one projection or the at least one recess, that the operating-mode switching member has at least a first and a second operating-mode position, and that the operating-mode switching member in accordance with the coding of the tool part occupies one of the at least two operating-mode positions. For example, by means of the operating-mode switching member a fluid flow or an energy supply of the drive unit elsewhere may be limited to prevent damage to the tool part.

It is therefore advantageous if the at least two operating-mode positions are associated with maximum actuating forces of the drive unit. For example, in a first operating-mode position a maximum driving force of the drive unit may be generated, in a second operating-mode position on the other hand only a reduced driving force, for example only a driving force corresponding to approximately 80 to 90% of the maximum force, may be generated.

It is advantageous if the operating-mode switching member is coupled to the control member and if the operating-mode switching member in at least one operating-mode position directly or indirectly deactivates at least one switching position of the control member. For example, the operating-mode switching member may be constructed in such a way that it mechanically or by means of control technology prevents the control member being moved into a switching position, in which with the drive unit a maximum force for actuating the movable tool may be generated.

A detailed explanation of the invention is provided by the following description of a preferred form of construction in connection with the drawings. The drawings show:

DETAILED DESCRIPTION OF THE INVENTION

Figure 1:
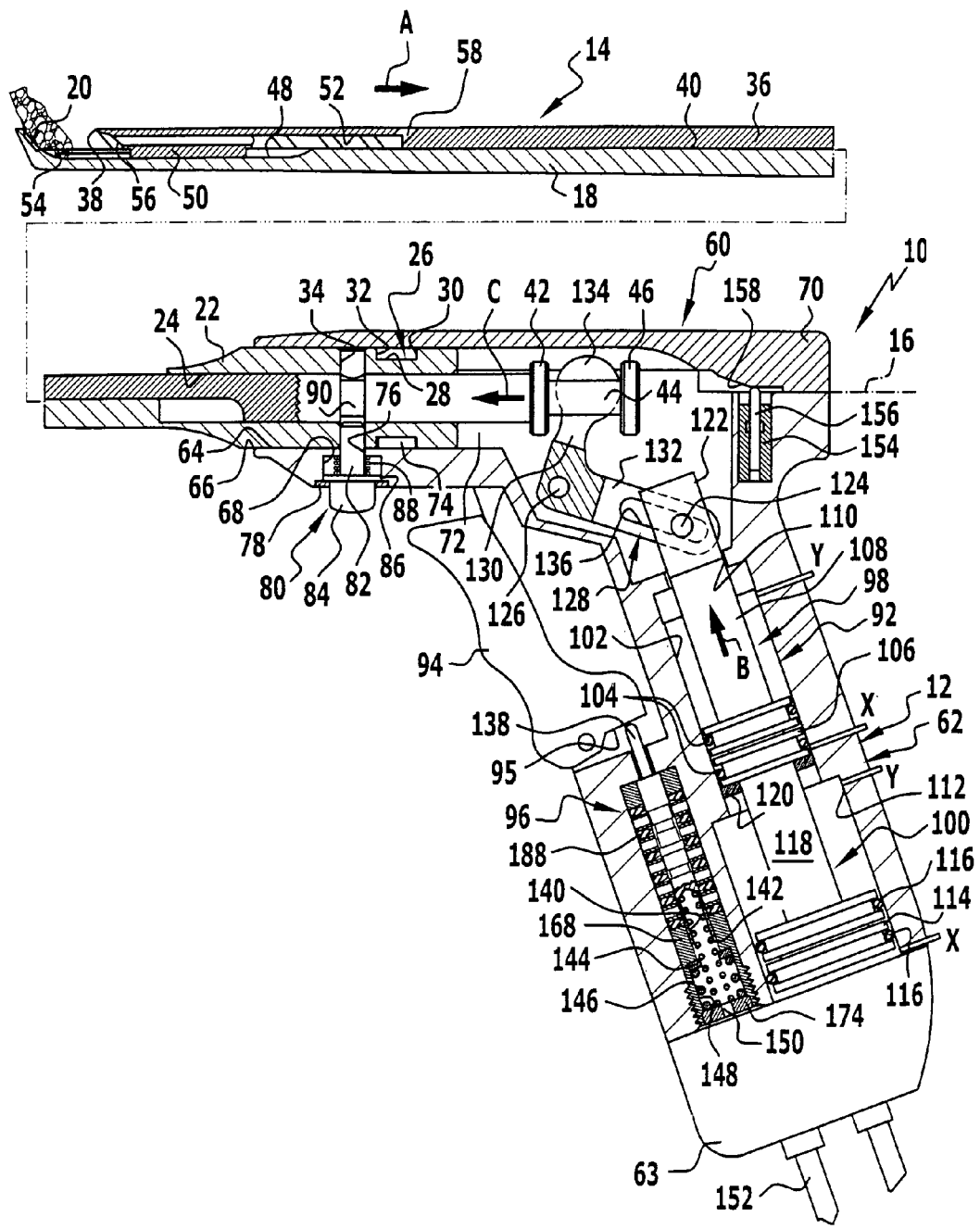
FIG. 1: a longitudinal sectional view through a bone punch in a non-actuated position.

FIGS. 1 to 7 show a surgical instrument according to, the invention in the form of a bone punch, which is provided as a whole with the reference character 10. The bone punch 10 comprises two basic sub-assemblies, namely a handling part 12 and a punching tool provided with the reference character 14.

The punching tool 14 comprises an elongate shank 18, which extends in a longitudinal direction 16 and carries on its distal end a cutting plate 20, which is inclined at an angle of approximately 45° relative to the longitudinal direction 16. A proximal end of the shank forms a coupling piece 22 in the form of an elongate cuboid, which is quadrilateral in cross section and has chamfered longitudinal edges. The coupling piece 22 is provided with a through-bore 24 that defines the longitudinal axis 16. There is further formed on the coupling piece 22 at a slight distance from the proximal end of the shank 18 a groove-like indentation 26 extending in peripheral direction, wherein a base of the indentation forms a quadrilateral 28. The quadrilateral 28 serves as a first coupling element for twist-proof connection of the punching tool 14 to the handling part 12. The coupling element (quadrilateral 28) simultaneously forms a kind of coding element for coding a specific type of tool part. A side wall 30 of the indentation 26 adjoining the quadrilateral 28 on the proximal side forms a stop acting in a distal direction. A side wall 32 adjoining the indentation 26 on the distal side forms a stop acting in a proximal direction.

On the distal side of the indentation 26 there are formed on the coupling piece 22 four identical securing bores 34, which extend in radial direction relative to the longitudinal axis 16 as far as the through-bore 24 through the coupling piece 22. The cuboidal coupling piece 22 moreover reduces in diameter at the distal side and at its end has a substantially circular-sleeve-like shape.

The punching tool 14 comprises a punch 36, which on its distal end carries a cutting edge 38, which is inclined relative to the longitudinal axis 16 by the same angle as the cutting plate 20. The punch 36 rests substantially along its entire length flat against a shank surface 40 of the shank 18. At the proximal end the punch 36 penetrates the through-bore 24 of the coupling piece 22. In this region the punch 36, which at the distal end is otherwise substantially cuboidal in cross section, is cylindrical in shape. Adjoining the cylindrical portion of the punch 36 at the proximal end is a quadrilateral, plate-shaped flange 42, which at the distal end delimits a coupling square 44 and forms a stop acting in proximal direction. Adjoining the coupling square 44 and forming an end of the punch 36 is a square end plate 46, which forms a stop acting in distal direction. The flange 42 moreover forms a stop, which acts in distal direction and strikes against the proximal end of the coupling piece 22 when the cutting edge 38 occupies its most distal position, i.e. rests against the cutting plate 20.

For stabilizing a movement of the punch 36 relative to the shank 18, in addition to the guide formed by the coupling piece 22 there is disposed on the distal end of the shank a guide groove 48, which widens in cross section away from the shank surface 40. Guided in the guide groove 48 is a guide projection 50, which protrudes from the punch 36 and extends parallel to the longitudinal axis 16 in proximal direction from the distal end of the punch 36. The guide projection 50 and the guide groove 48 are constructed in a substantially corresponding manner, for example they may have a dovetail shape.

Starting from the cutting edge 38 the punch 36 is provided with a blind-hole-like recess, which extends parallel to the longitudinal axis 16 and serves as a tissue reservoir 52 for tissue removed by the bone punch 10. Tissue 54 that has been punched out by the cutting edge is pushed into the tissue reservoir 52 through a distal opening 56 thereof and, upon further punching-out of tissue 54, is advanced in proximal direction, i.e. in the direction of the arrow A in FIG. 1. In the embodiment illustrated in the drawings, for emptying the tissue reservoir 52 there is provided in the punch 36 a discharge opening 58, which is formed by a bore of the punch 36 that extends obliquely relative to the longitudinal axis and establishes a fluid connection between the tissue reservoir 52 and an area surrounding the punching tool 14. Tissue 54 that has been punched out and stored in the tissue reservoir 52 may be discharged out through the discharge opening 58. In an alternative, non-illustrated form of construction of the invention, there may be provided in the punch 36 an ejector in the form of a rod, which is displaceable parallel to the longitudinal axis 16 and by means of which, starting from the proximal end of the tissue reservoir 52, tissue stored therein may be expelled in distal direction out through the opening 56.

The handling part 12 of the bone punch 10 is designed substantially in the form of a housing similar to a pistol grip. It comprises an elongate cuboidal upper housing part 60, which extends parallel to the longitudinal axis 16 and has an opening 66 facing in distal direction and forms a substantially elongate, cuboidal receiving chamber 64 for the coupling piece 22 of the shank 18. Transversely thereof and with a slight inclination in proximal direction a handle 62 projects from the upper housing part 60.

The upper housing part 60 comprises a sliding cover 70, which is guided parallel to the longitudinal axis 16 by means of two guides in the form of rib-like projections on either side in longitudinal grooves in side walls 72 of the upper housing part 60 that extend parallel to the longitudinal axis 16. The sliding cover 70 in its most distal position completely covers the receiving chamber 64 and in its most proximal position predominantly clears the receiving chamber 64, thereby forming an insertion opening, through which the coupling piece 22 may be inserted into the receiving chamber 64 in a direction transversely of the longitudinal axis 16.

On inner sides of the side walls 72 two coupling projections 74, which face one another and form a second coupling element, are positioned opposite one another. They are designed substantially in the form of flat cuboids, the dimensions of which are so selected that the two coupling projections 74 may engage between the side walls 30 and 32 into the indentation 26 and rest substantially against the quadrilateral 28. By this means, the punching tool 14 is fixed axially on the handling part 12.

Figure 3:
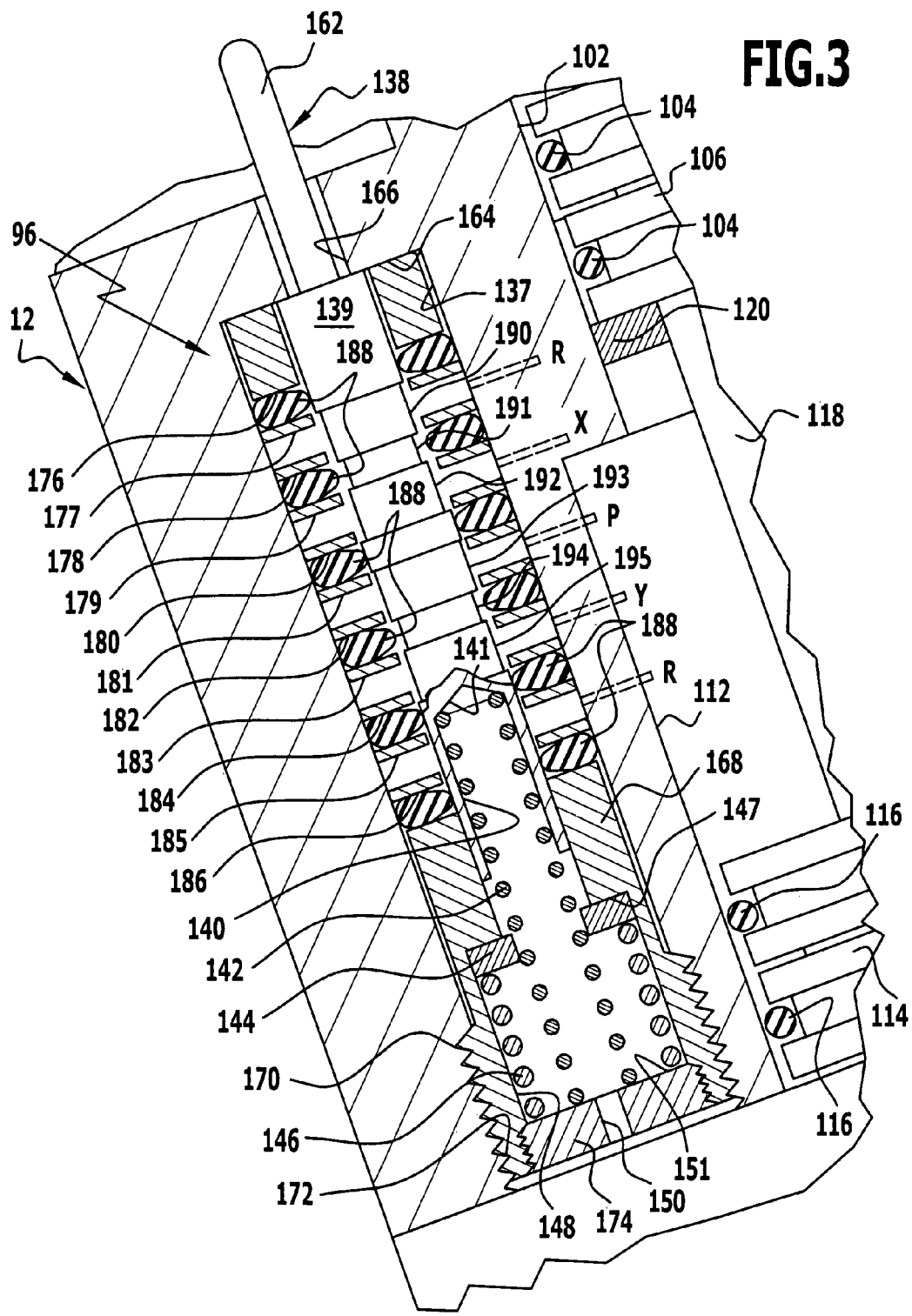
FIG. 3: an enlarged detail of a switching valve illustrated in FIG. 2.
Figure 4:
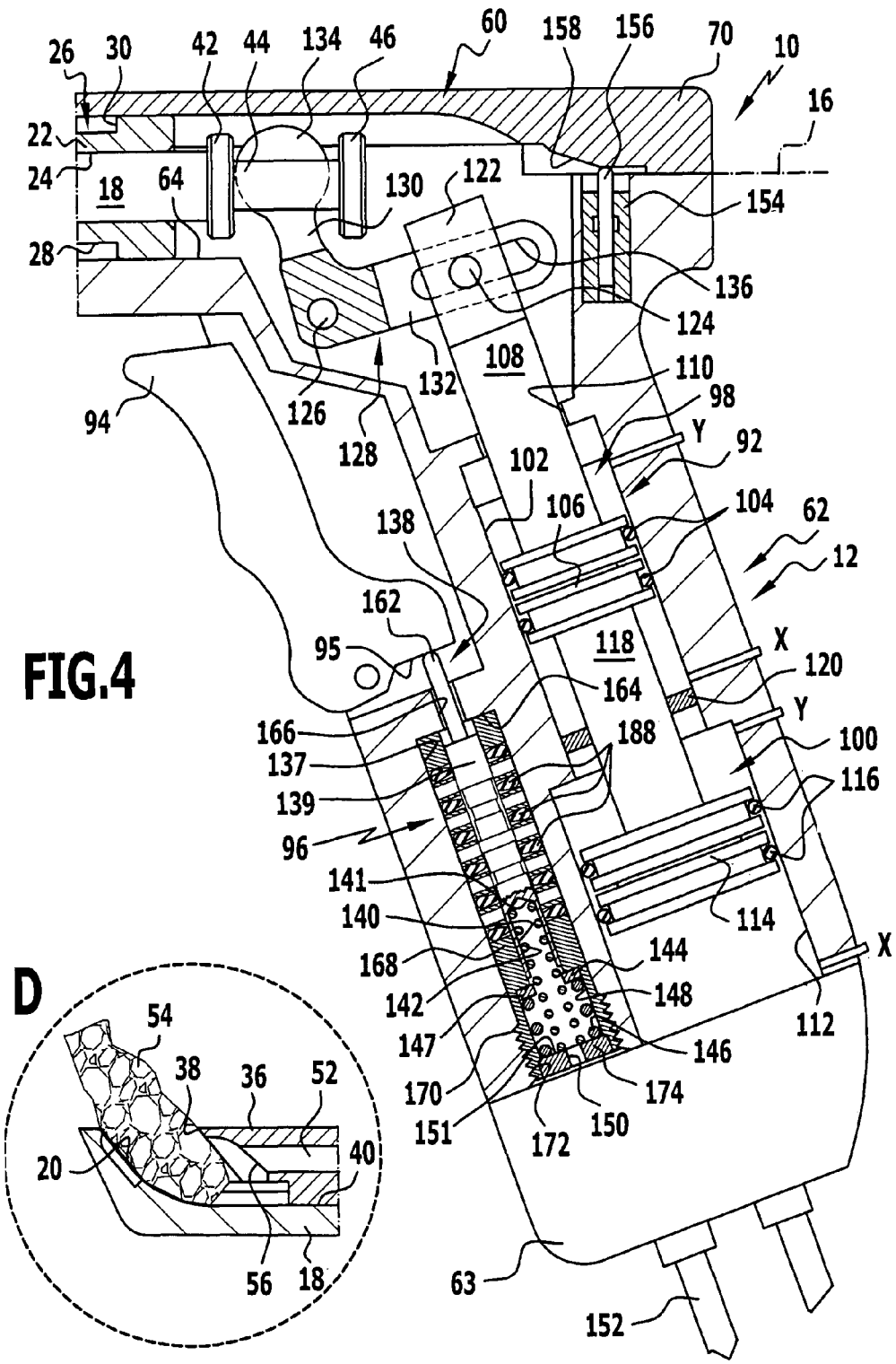
FIG. 4: a view similar to FIG. 2 of the instrument in a first working position.

As may be seen particularly well in FIG. 1, on the distal side of the coupling projections 74 the upper housing part 60 is provided at its underside with a downwardly open, cup-shaped indentation 68, which in the direction of the receiving chamber 64 is connected by a bore 76. The indentation 68 in the direction remote from the receiving chamber 64 is provided from the outside with a disc 78, which forms a radially inwardly projecting flange. The indentation 68 is used to receive a securing knob 80, which comprises a cylindrical bolt 82 that penetrates the bore 76 and carries a head 84, wherein in the transition region between the head 84 and the bolt 82 a radially outwardly projecting annular flange 86 is formed. Adjacent to the bore 76 there is supported in the indentation a helical spring 88, which surrounds the bolt 82 and is supported by its other end against the underside of the head 84. As a result, the annular flange 86 in a basic or inoperative position, such as is illustrated in FIGS. 1 and 3, is pressed against the disc 78. The securing knob 80 may be moved counter to the action of the helical spring 88 in the direction of the receiving chamber 64, as is indicated in FIG. 4 by the arrow E. The securing knob 80 is moreover disposed in such a way that, when the coupling piece 22 is inserted into the receiving chamber 64, in the basic position, in which the helical spring 88 presses the annular flange 86 against the disc 78, the securing knob 80 substantially positively fills the securing bore 34. In the inserted state of the coupling piece 22, however, the securing knob 80 may only be moved in the direction of the receiving chamber 64 when an annular groove 90, which in peripheral direction surrounds the cylindrical part of the punching tool 14 that penetrates the through-bore 24, overlaps with the security bores 34 in radial direction. As is shown in FIG. 1, this is the case when the punching tool 14 is in its most proximal position relative to the shank 18, i.e. when there is the maximum distance between the cutting edge 38 and the cutting plate 20. If the securing knob 80 is then pressed, then, as illustrated in FIG. 4, a front end of the bolt 82 engages into the annular groove 90, thereby preventing a movement of the punching tool 14 parallel to the longitudinal axis 16.

A pneumatic drive device provided as a whole with the reference character 92 is disposed substantially in and/or on the handle 62. The drive device 92 comprises an actuating lever 94, which is disposed at a side of the handle 62 facing in distal direction, directly underneath the upper housing part 60, and mounted pivotably about a swivel axis running transversely to the longitudinal axis 16, a switching valve 96 that is actuable by means of the actuating lever 94, and a drive unit that comprises a first pneumatic cylinder 98 and a second pneumatic cylinder 100.

The two pneumatic cylinders 98 and 100 are each of a double-acting design, wherein the first pneumatic cylinder 98 comprises a cylindrical piston chamber 102, in which a piston 106 sealed by means of two sealing rings 104 is displaceable parallel to the axis of symmetry of the piston chamber 102. The piston chamber 102, in an identical manner to the handle 62, is slightly inclined relative to the longitudinal axis 16. Projecting from the piston 106 and directed towards the receiving chamber 64 is a piston rod 108, which is guided in a piston bore 110 that connects the piston chamber 102 to the receiving chamber 64. A piston chamber 112 directly adjoins the piston chamber 102, namely with a slightly larger inside diameter. In this, a displaceably mounted piston 114 is sealed by means of two sealing rings 116 and connected by a piston rod 118 directly to the piston 106. The two pneumatic cylinders 98 and 100 therefore form an, as a whole, rotationally symmetrical piston/cylinder unit. The piston chambers 102 and 112 are separated by a sealing disc 120 that is penetrated by the piston rod 118. Each of the two pneumatic cylinders 98 and 100 is provided with two ports X and Y, through which the pistons 106 and 114 can be acted upon by compressed air. The ports X are in this case disposed in each case at an end of the respective piston chamber 102 or 112 remote from the receiving chamber 64, so that the pistons 106 and 114 upon loading with compressed air through the ports X are moved in the direction of the arrow B in FIG. 1. The ports Y are disposed in each case at the other end of the two piston chambers 102 and 112, so that the pistons 106 and 114 when acted upon by compressed air through the ports Y are moved in an opposite direction to the arrow B.

Adjoining the piston rod 108 and directed towards the receiving chamber 64 is a cuboidal extension 122, which carries a drive pin 124 that projects on both sides transversely of the longitudinal axis 16 and of the longitudinal axis of the piston rod 108. Extending parallel to the drive pin 124 and disposed in the transition region of the upper housing part 60 to the handle 62 is a bearing shaft 126, which is used to mount an L-shaped angle lever 128. A first lever arm 130 of the angle lever 128 is directed substantially towards the receiving chamber 64, a second lever arm 132 is oriented in proximal direction substantially parallel to the receiving chamber 64.

Free ends of the two lever arms 130 and 132 are slotted in each case in the direction of the bearing shaft 126 parallel to a plane of symmetry of the bone punch 10, so that the free ends are each of a U-shaped design. The angle lever 128 is disposed in such a way that the slotted free end of the first lever arm 130, which is designed in the form of two disc-shaped drivers 134, engages on both sides around the coupling square 44 between the flange 42 and the end plate 46 but does not project laterally beyond the flange 42 and the end plate 46. The first lever arm 130 is moreover tapered in such a manner relative to the drivers 134 that only these may come into contact with the flange 42 and the end plate 46. The slotted end of the second lever arm 132 is provided with in each case one elongate-hole-like slot 136 and surrounds the extension 122, wherein the drive pin 124 engages into the slots 136 and is guided therein.

The second lever arm 132 is approximately twice as long as the first lever arm 130. The angle lever 128 therefore forms, on the one hand, a force deflection unit for deflecting a driving force, which may be generated in the direction of the arrow B in FIG. 1 by the pneumatic cylinder 98 and 100, in a drive direction extending parallel to the longitudinal axis 16 and symbolized by the arrow C in FIG. 1. At the same time, the angle lever 128 also forms a mechanical advantage unit, by means of which the driving force generated by the piston/cylinder unit is doubled owing to the length ratio of the lever arms 130 and 132.

The pneumatic cylinders 98 and 100 are controlled by means of the switching valve 96, which is disposed in the region of an end 63 of the handle 62 facing away from the receiving chamber 64, in an elongate cylindrical hollow chamber 137 extending parallel to the second pneumatic cylinder 100, and comprises a plunger 138, which is actuable by the actuating element 94 and displaceable parallel to the pistons 106 and 114. The switching valve 96 as a whole is of a rotationally symmetrical design, wherein the plunger 138 comprises an elongate cylindrical plunger body 139 that penetrates the switching valve 96. An end of the plunger 138 facing towards the actuating lever 94 forms a plunger tip 162, which is reduced in one stage in diameter and penetrates a bore 166, which penetrates the hollow chamber 137 at an inner end face 164, and rests directly against an actuating surface 95 of the actuating lever 94 that faces the end 63. The bore 166 has a diameter smaller than an outside diameter of the plunger body 139, so that the end face 164 forming an inner annular surface forms a stop for the plunger body 139.

An end of the plunger body 139 remote from the actuating element 94 is provided with a blind hole 140 that is open in the direction of the end 63, so that this end of the plunger body 139 is designed like a sleeve. A helical spring 142 is supported against a blind hole base 141 of the blind hole 140 that faces the end 63.

A sleeve-like valve insert 168 is inserted into the hollow chamber 137, filling the entire length thereof, and is penetrated by the plunger body 139 along the axis of symmetry thereof. Adjacent to its end facing the end 63, the valve insert 168 is provided with a short externally threaded portion 170, which is designed to correspond with a short internally threaded portion 172 adjacent to an end of the hollow chamber 137 facing the end 63. The valve insert 168 is screwed by means of the externally threaded portion 170 into the hollow chamber 137 and is therefore axially fixed.

An inside diameter of the valve insert 168 roughly corresponds to a maximum outside diameter of the plunger body 139. The inside diameter of the valve insert 168 is moreover widened in one stage roughly along the length of the externally threaded portion 170, thereby forming a valve chamber 148, the diameter of which is slightly larger than a maximum outside diameter of the plunger body 139. The valve chamber 148 is closed in the direction of the end 63 by a cover 174, the inner side of which forms a base 151 facing towards the actuating lever 94.

The base 151 is interrupted centrally by an inlet opening 150 in the form of a bore. The one-stage widening in the interior of the valve insert 168 forms an annular wall 147 facing towards and extending parallel to the base 151. This annular wall 147 forms a stop for a disc 144, the outside diameter of which corresponds to the inside diameter of the valve chamber 148 and which has a circular through-hole, the diameter of which is slightly smaller than a maximum outside diameter of the plunger body 139. The previously mentioned helical spring 142 is supported by its other end against the base 151 and surrounds the inlet opening 150 of the valve chamber. The maximum outside diameter of the helical spring 142 is so selected that the spring penetrates the through-hole of the disc 144 without play. The helical spring 142 presses the plunger 138 in the direction of the actuating lever 94, so that the switching valve 96 in the non-actuated state rests with its plunger tip 162 against the actuating surface 95 of the actuating lever 94. A further helical spring 146 is supported by one end against the disc 144 and by the other end against the base 151 and surrounds the helical spring 142. The helical spring 146 has a spring constant that is many times greater than that of the helical spring 142.

Figure 2:
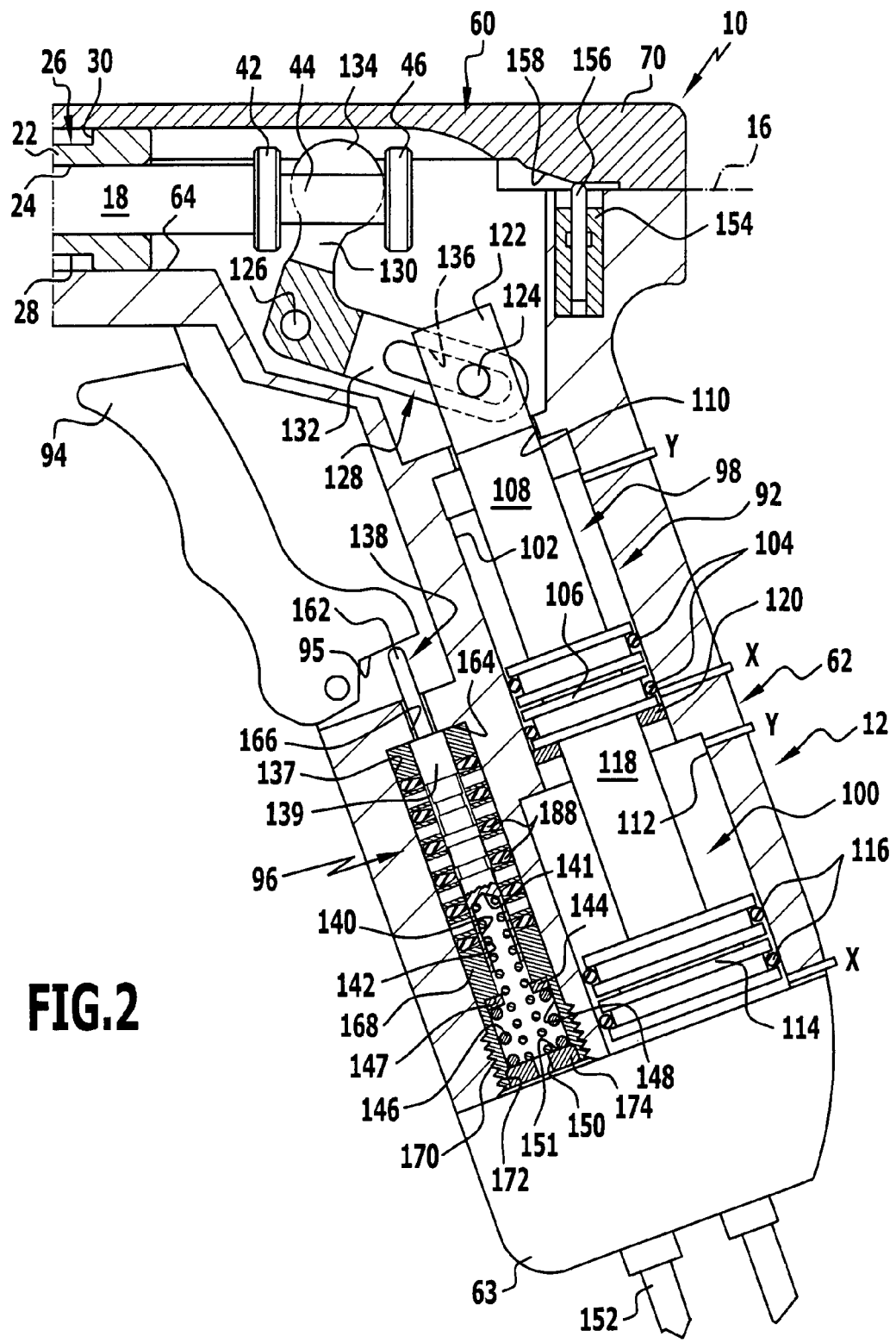
FIG. 2: an enlarged view of the handling part of the instrument in FIG. 1.
Figure 5:
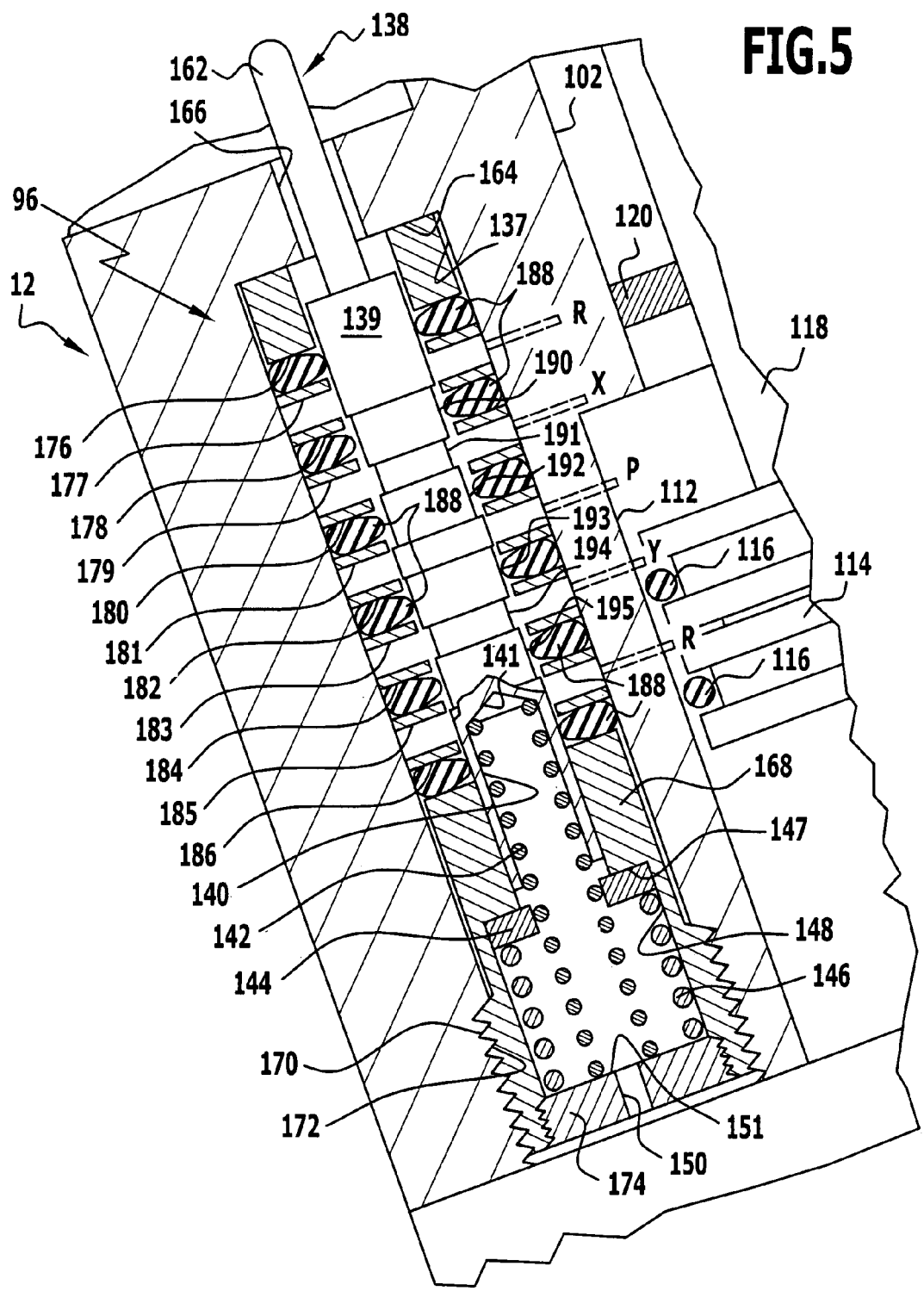
FIG. 5: a view similar to FIG. 3, but in the first working position.
Figure 6:
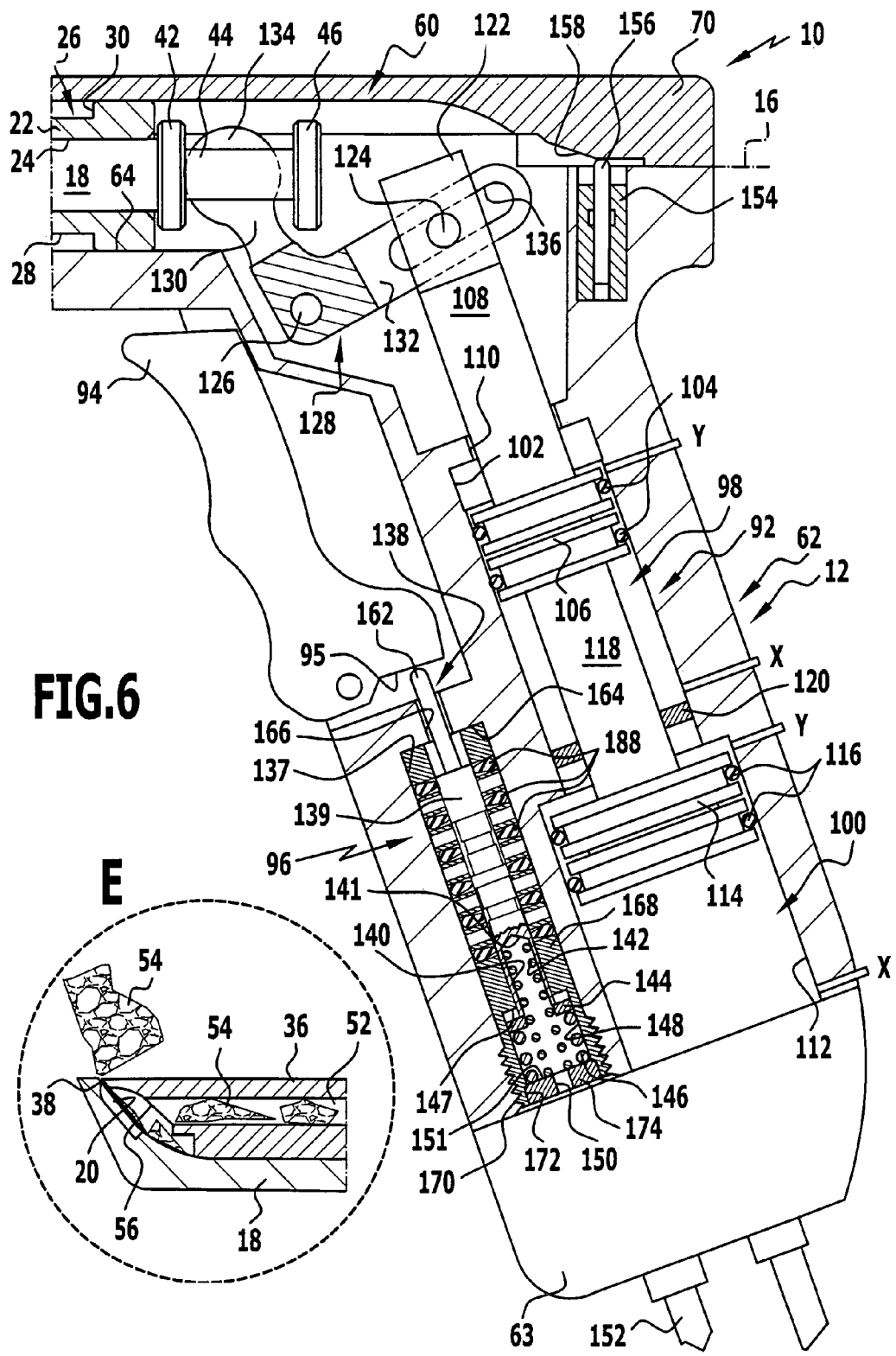
FIG. 6: a view similar to FIG. 2 in a second working position.
Figure 7:
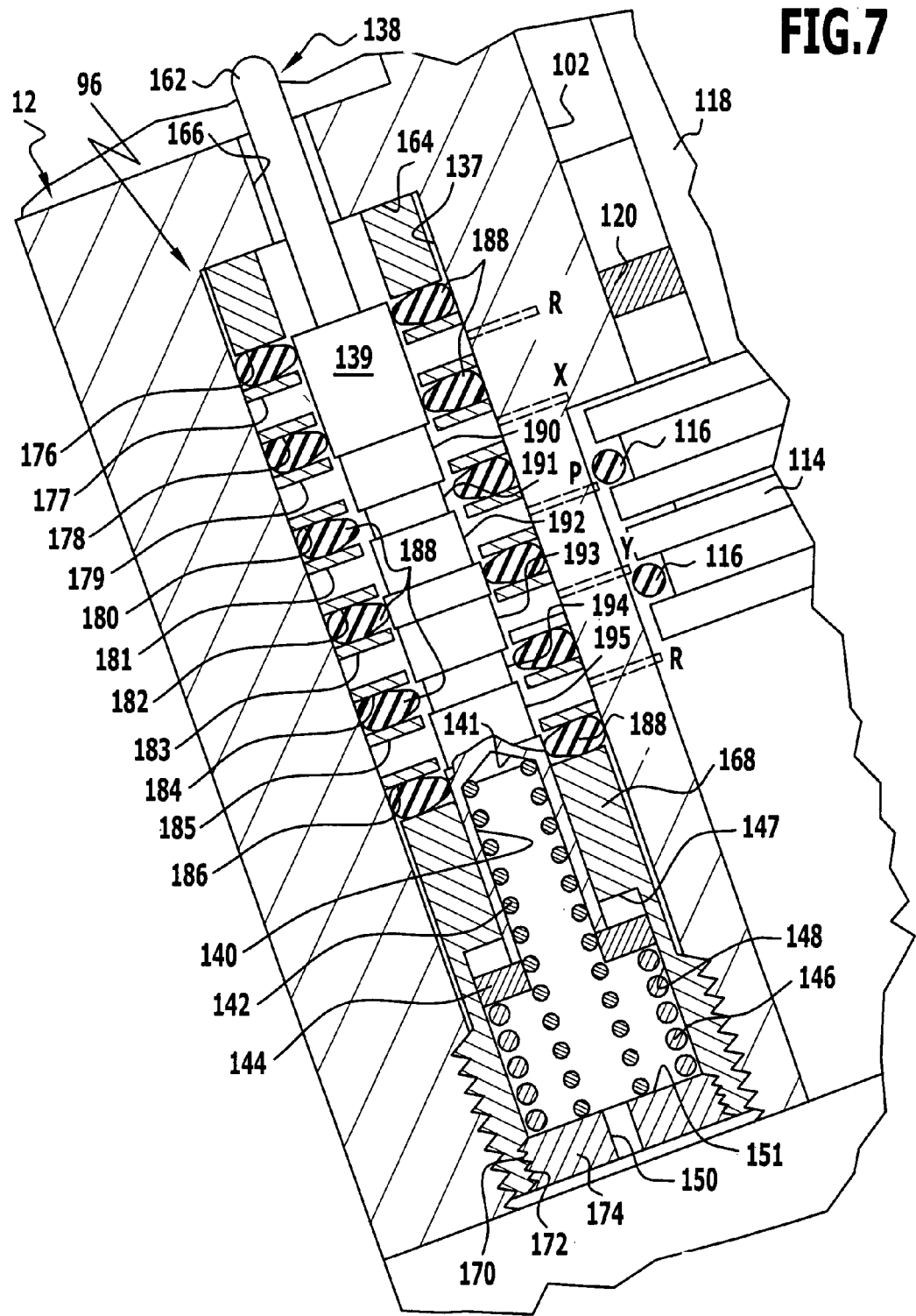
FIG. 7: a view similar to FIG. 3, but in the second working position.

The plunger 138 may be moved from a non-actuated position, such as is shown in FIGS. 1 to 3, counter to the action of the helical spring 142 towards the disc 144 until the sleeve-like end of the plunger body 139 strikes against the disc 144. The switching valve 96 then occupies a first switching position, such as is shown in FIGS. 4 and 5. If the actuating lever 94 is pivoted further, the sleeve-like end of the plunger body 139 drives the disc 144 then also counter to the action of the helical spring 146. This second switching position is shown in FIGS. 6 and 7. Thus, upon actuation of the actuating lever 94 an operator may infer a switching position of the switching valve 96 from the resetting forces generated by the helical springs 142 and 146 and exerted on the plunger 138. As the spring constant of the helical spring 146 is many times greater than that of the helical spring 142, an operator receives tactile feedback that a transfer from the first switching position to the second switching position has occurred. Starting from its end resting against the end face 164, the valve insert 168 is provided with altogether eleven identical annular grooves 176 to 186, wherein there is inserted into each of the even-numbered annular grooves 176, 178, 180, 182, 184, 186 a sealing ring 188 that forms a sealing lip for the plunger body 139.

The plunger body 139 is provided with an annular groove system, which is described with reference to FIG. 3. In the basic position of the switching valve 96 illustrated in FIG. 3, the sealing ring 188 inserted into the annular groove 176 seals off the plunger body 139 in the direction of the bore 166. At the level of the annular groove 177 an outside diameter of the plunger body 139 is reduced in one stage and forms an annular groove 190. Opposite the sealing ring 188 inserted in the annular groove 178, the outside diameter of the plunger body 139 is reduced once more in one stage and forms an annular groove 191. The outside diameter of the plunger body 139 then increases again in one stage and forms an annular groove 192 that lies opposite the annular groove 179. The sealing ring 188 inserted into the annular groove 180 again rests sealingly against the maximum outside diameter of the plunger body 139. This is in turn adjoined by an annular groove 193 of the plunger body 139 that is reduced in its outside diameter in one stage but has a larger outside diameter than the identical annular grooves 190 and 192. Lying opposite the sealing ring 188 inserted into the annular groove 182 is a further annular groove 194, the outside diameter of which roughly corresponds to that of the annular grooves 190 and 192. This is in turn adjoined by an annular groove 195, which corresponds to the annular groove 193 and is formed opposite the annular groove 184. The sealing ring 188 inserted into the annular groove 184 once more completely seals off the plunger body 139.

The odd-numbered annular grooves 177, 179, 181, 183 and 185 are provided with air inlet openings X, Y and P, which are diagrammatically represented by dashes in the drawings and are connected to the two pneumatic cylinders 98 and 100 as well as to a non-illustrated compressed air source in the following manner. The annular groove 181 is provided with an inlet opening denoted by P, which is connected to the non-illustrated compressed air source. The inlet opening X provided at the annular groove 179 is connected to the two inlet openings of the pneumatic cylinders 98 and 100, which are denoted there likewise by X. Furthermore, the annular groove 183 is provided with an inlet opening denoted by Y, which is likewise connected to the inlet openings denoted by Y of the pneumatic cylinders 98 and 100. There are moreover connected to the annular grooves 177 and 185 inlet openings that are both denoted by R. These form ventilation openings, through which compressed air may escape from the system.

The three possible switching positions of the switching valve 96 are described in detail below. As has already been described, in the non-actuated position of the actuating lever 94 illustrated in FIGS. 1 to 3, a so-called inoperative or basic position, the inlet openings X and R of the hollow chamber 137 that are connected to the annular grooves 177 and 179 are fluidically connected. As a result, the two pneumatic cylinders 89 and 100 are ventilated through their inlet openings X. The inlet openings P and Y connected to the annular grooves 181 and 183 are likewise fluidically connected by the annular chambers defined by means of the annular grooves 193, 194 and 195. Thus, the compressed air source is connected via the switching valve 96 to the inlet openings Y of the pneumatic cylinders 98 and 100 in such a way that the two pneumatic cylinders 98 and 100 are moved jointly into their end position counter to the direction indicated by the arrow B. The instrument therefore occupies a retaining position, which corresponds to the inoperative or basic position. There is a maximum distance between the cutting edge 38 and the cutting plate 20.

When the actuating lever 94 is pivoted towards the handle 62, the plunger 138 is moved in the direction of the disc 144. The switching valve 96 then occupies the first switching position illustrated in FIGS. 4 and 5. As a result of the differently selected outside diameters of the annular grooves 190 to 195, on the one hand the annular grooves 181, 179 and 177 are connected to one another so that compressed air may flow through the inlet P of the switching valve 96 and through the inlet X at the annular groove 179 to the inlets X of the two pneumatic cylinders 98 and 100, these however being connected via the connection by means of the annular grooves 190, 191 and 192 also to the ventilation opening R of the annular groove 177. On the other hand, the inlet P at the annular groove 181 is fluidically connected by the annular grooves 193, 194 and 195 to the inlet Y at the annular groove 183 and to the inlet R at the annular groove 185. Compressed air may therefore flow through the inlets Y into the pneumatic cylinders 98 and 100. As a result of the specially selected outside diameters of the annular grooves 190, 191, 192 as well as 193, 194 and 195, the fluid flows into the inlets X and Y, with which the two pneumatic cylinders 98 and 100 are loaded, are distributed in such a way that a resulting driving force acting in the direction of the arrow B corresponds to approximately 20% of a maximum propulsion force that may be generated by the two pneumatic cylinders 98 and 100. This force, as is illustrated in the area D outlined by dashes in FIG. 4, is not sufficient to cut through tissue 54 that is to be removed but is sufficient to move the cutting edge 38 into abutment with the tissue 54.

If however the actuating lever 94 is moved further in the direction of the handle 62 as far as the stop, the plunger 138 is transferred into the second switching position, which is illustrated in FIGS. 6 and 7. The sealing rings 188 inserted in the annular grooves 178 as well as 182 and 186 completely seal off the plunger body 139, thereby establishing, on the one hand, a fluid connection between the inlet opening X connected to the annular groove 179 and the inlet opening P connected to the annular groove 181 and, on the other hand, a fluid connection between the inlet opening Y connected to the annular groove 183 and the inlet opening R connected to the annular groove 185. In this switching position both pneumatic cylinders 98 and 100 are loaded through their inlet openings X with compressed air from the compressed air source. A loading with compressed air in the opposite direction is not possible because the inlet openings Y are connected to the ventilation opening R, which is connected to the annular groove 185, and are therefore ventilated. Both pneumatic cylinders 98 and 100 are therefore driven in the direction of the arrow B in FIG. 1, thereby allowing a maximum driving force to be generated and transmitted to the punch 36.

In order further to improve tactile feedback for an operator of the bone punch, the inlet opening X connected to the annular groove 179 may be connected also to the inlet opening 150 of the valve chamber 148. If in the second switching position, such as is illustrated in FIGS. 6 and 7, both of the pneumatic cylinders 98 and 100 are loaded with compressed air of maximum pressure, then this pressure acts also in the same direction as the helical springs 142 and 146, with the result that a surgeon has to apply an increased actuating force in order to maintain the second switching position of the actuating lever 94.

There now follows a detailed description of the mode of operation of a slightly modified form of construction of the drive device 92 of the instrument.

In a non-actuated position of the actuating lever 94, the first pneumatic cylinder 98 is loaded with compressed air through its inlet Y in such a manner that the piston 106 is moved against the sealing disc 120. The bone punch then occupies its open position, i.e. the driver 134 holds the end plate 46 of the punch 36 in its most proximal position. There is a maximum distance between the cutting edge 38 and the cutting plate 20.

If the actuating lever 94 is moved counter to the helical spring 142 without the plunger 138 striking against the disc 144, only the piston 106 is moved in the direction of the arrow B in FIG. 1 by means of pressure loading through the inlet X between the piston 106 and the rotatable disc 120. A ratio of the effective cross sections of the first pneumatic cylinder 98 and the second pneumatic cylinder 100 is approximately 1:4, so that initially only a driving force amounting to approximately 20% of a maximum possible driving force is generated and transmitted via the angle lever 128 to the punch 36. The thus reduced force acting upon the punch 36 is typically insufficient to cut through tissue 54, for example bone parts, that are to be removed. The force, as is illustrated in the area D outlined by dashes in FIG. 4, is only sufficient to bring the cutting edge 38 up to the tissue. In this first actuating position of the actuating lever, an operator of the bone punch 10 may therefore lay the cutting plate 20 in a desired manner against the tissue 54 to be removed, without the tissue 54 actually being cut through at this stage.

Once the cutting position has been determined, the actuating lever 94 may be fully depressed. The plunger 138 is then moved also counter to the helical spring 146, the operator sensing this because of the increased actuating force that has to be applied in order to pivot the actuating lever 94. The switching valve 96 then occupies a switching position, in which both the first pneumatic cylinder 98 and the second pneumatic cylinder 100 are loaded with compressed air through their inlets X, namely in such a way that both pistons 106 and 114 are moved in the direction of the arrow B. A maximum force of the drive device 92 is therefore transmitted via the angle lever 128 to the punch 36 and is capable of cutting through tissue 54 in a desired manner. In this position, inlets Y of the pneumatic cylinders 98 and 100 that are not loaded with compressed air are ventilated in each case.

When load is removed from the actuating lever 94, the helical springs 142 and 146 press the plunger 138 back into its basic position, the punch 36 is then loaded once more by pressure loading of the pneumatic cylinder 98 in an opposite direction to the arrow B, with the result that the punch 36 is transferred from its cutting position illustrated in FIGS. 6 and 7, via its intermediate position illustrated in FIGS. 4 and 5, back into its basic position illustrated in FIG. 1, i.e. its most proximal position.

So much for the mode of operation of the slightly modified form of construction of the drive device 92.

To rule out inadvertent actuation of the drive device 92 as a result of an operator pressing the actuating lever 94, in the proximal region of the upper housing part 60 a safety valve 154 is disposed. The safety valve 154 comprises a valve plunger 156, which is mounted so as to be displaceable transversely of the longitudinal axis 16 and is spring-biased against an inner side of the cover 70. When, as is illustrated in FIG. 1, the cover 70 is closed, the valve plunger 156 occupies a position, in which it establishes a fluid connection between the compressed-air supply line 152 and the inlet opening 150 of the switching valve 96. However, when the cover 70 is opened, the end of the valve plunger 156 projecting from the safety valve 154 slides along a stop slope 158 on the inner side of the cover 70, with the result that the spring-biased valve plunger 156 is moved further out of a body of the safety valve 154. The safety valve 154 therefore changes its switching position and then interrupts a connection between the compressed-air supply line 152 and the inlet opening 150 of the switching valve 96, with the result that an actuation of the actuating lever 94 remains ineffective because the drive device 92 is therefore cut off from the compressed air source. It is only when the sliding cover 70 is completely closed again that the valve plunger 156 is pressed far enough into the body of the safety valve 154 for the safety valve 154 to return to the switching position, in which the compressed-air supply line 152 is fluidically connected to the inlet opening 150 of the switching valve 96.

Should the bone punch 10 require cleaning while in use, for example because tissue 54 has become jammed between the cutting edge 38 and the cutting plate 20, there is no need for a surgeon to let go of the bone punch 10. A person assisting the surgeon may clean a gap between the cutting edge 38 and the cutting plate 20 without running any risk of being injured, even if the operator actuates the actuating lever 94. In a non-actuated position of the actuating lever 94, the annular groove 90 and the securing bores 34 overlap. This is illustrated in FIG. 1. The person assisting the surgeon may therefore press the securing knob 80 counter to the action of the helical spring 88 so that the bolt 82 engages into the annular groove 90, in the manner illustrated in FIG. 4. A movement of the punch 36 in distal direction is therefore prevented, even in the event of the surgeon pressing the actuating lever 94. Once the tissue part 54 to be removed has been cut off and removed, the person assisting the surgeon may let go of the securing knob 80 and the surgeon may proceed with the operation. The described cleaning operation is particularly easy to carry out because the securing knob 80 is disposed far enough away from the actuating lever 94, in particular on the distal side thereof, for the securing knob 80 to be always freely accessible to the person assisting the surgeon.

By virtue of the special development of the coupling piece 22, in particular by virtue of providing the quadrilateral 28, it is possible to connect the punching tool 14 in four different positions to the handling part 12. In FIGS. 1 to 5 the punching tool 14 is connected to the handling part 12 in such a way that a gap between the cutting plate 20 and the cutting edge 38 is facing upwards. The two parts of the bone punch 10 may however also be connected to one another in such a way that the gap is facing downwards or towards one of the two sides of the bone punch 10. To alter a position of the punching tool 14 relative to the handling part 12, the sliding cover 70 merely has to be displaced in proximal direction until the receiving chamber 63 may be opened and the punching tool 14 removed. The punching tool 14 may then be rotated through 90°, 180° or 270° and inserted back into the receiving chamber 64. Displacing the cover 70 in distal direction closes the receiving chamber 64 and moreover secures the coupling piece 22 and hence the punching tool 14 on the handling part 12.

The invention claimed is:

1. Surgical instrument, comprising:
a handling part, and
a tool part, the tool part comprising at least one movably mounted tool, which is actuable by means of a force-transmitting and/or actuating mechanism that is operable from the handling part, and
the force-transmitting and/or actuating mechanism comprising a fluid-operable drive unit which comprises a linear drive comprising two coupled, separately controllable fluid cylinders, each fluid cylinder having a respective piston arranged therein,
wherein with the drive unit in a first driving position the movably mounted tool is subjected to a first actuating force in an actuating direction and in at least a second driving position is subjected to at least a second actuating force in the actuating direction.

2. Instrument according to claim 1, wherein with the drive unit in a third driving position the movably mounted tool can be subjected to a third actuating force in the actuating direction.

3. Instrument according to claim 2, wherein the third actuating force corresponds to the sum of the first and second actuating forces.

4. Instrument according to claim 1, wherein a ratio of the first and second actuating forces lies in a range of 4:1 to 9:1.

5. Instrument according to claim 1, wherein the two fluid cylinders have different effective cross sections.

6. Instrument according to claim 5, wherein a ratio of the effective cross sections lies in a range of 4:1 to 9:1.

7. Instrument according to claim 1, wherein the two fluid cylinders are pneumatic and/or hydraulic cylinders.

8. Instrument according to claim 1, wherein at least one of the two fluid cylinders is a double-acting fluid cylinder.

9. Instrument according to claim 1, wherein the instrument is designed for the removal of bone, cartilage or similar tissue, and the instrument further comprises a shank, which extends in a longitudinal direction and carries on its distal end a cutting plate, which is disposed transversely of the longitudinal direction or inclined relative to the longitudinal direction,
wherein the movably mounted tool is a cutting element mounted displaceably on the shank and carrying on its distal end a cutting edge, which is directed towards the cutting plate and is movable towards the cutting plate for the cutting of tissue.

10. Instrument according to claim 9, wherein:
there is disposed on the proximal end of the shank a first coupling element for detachable, positive connection to the force-transmitting and/or actuating mechanism,
the force-transmitting and/or actuating mechanism has a second coupling element corresponding to the first coupling element, and
the first coupling element is a polygon, outer faces of which are directed radially outwards from a longitudinal axis of the shank.

11. Instrument according to claim 10, wherein the polygon is a quadrilateral, a hexagon or an octagon.

12. Instrument according to claim 9, wherein the shank at the proximal end is shaped like a sleeve and the cutting element penetrates the sleeve-like end of the shank.

13. Instrument according to claim 9, wherein the cutting element at the proximal end carries a third coupling element, which is detachably connectable to a drive element of the force-transmitting and/or actuating mechanism, and the third coupling element is adjoined by stops acting in the longitudinal direction of the shank.

14. Instrument according to claim 1, wherein in an inoperative position of the instrument, in which no actuating force is exerted by the force-transmitting and/or actuating mechanism in the actuating direction on the tool, a retaining force may be exerted on the tool by the force-transmitting and/or actuating mechanism in a retaining direction opposite to the actuating direction.

15. Instrument according to claim 14, wherein the force-transmitting and/or actuating mechanism comprises an actuating member for actuating the drive unit, the actuating member is movable from an non-actuated basic position, in which the instrument occupies the inoperative position, into a first activation position, in which the drive unit occupies the first driving position, and into at least a second activation position, in which the drive unit occupies the second driving position.

16. Instrument according to claim 15, wherein the actuating member is held under spring bias in the basic position.

17. Instrument according to claim 15, wherein the actuating member is mounted pivotably.

18. Instrument according to claim 15, wherein:
in the first activation position a first resetting force acts upon the actuating member,
in the second activation position a second resetting force acts upon the actuating member, and
the second resetting force is greater than the first resetting force.

19. Instrument according to claim 18, wherein the second resetting force is at least twice as great as the first resetting force.

20. Instrument according to claim 18, wherein for generating the first and second resetting force there is provided a resetting unit comprising a first elastic resetting member and a second elastic resetting member.

21. Instrument according to claim 20, wherein at least one of the first resetting member and the second resetting member is a spring element.

22. Instrument according to claim 20, wherein the resetting unit is configured to act directly or indirectly upon a control member for controlling the drive unit or upon the actuating member.

23. Instrument according to claim 15, wherein a control member is provided for controlling the drive unit and the actuating member acts directly or indirectly upon the control member.

24. Instrument according to claim 23, wherein the control member comprises at least one control valve.

25. Instrument according to claim 24, wherein the at least one control valve has at least three different switching positions.

26. Instrument according to claim 24, wherein:
the two fluid cylinders are double-acting fluid cylinders,
the control valve comprises a valve plunger with a valve body,
on the valve body there is provided at least one port connectable to a fluid source and two ports for each double-acting fluid cylinder,
in a first position of the valve plunger at least one of the fluid cylinders can be loaded with fluid in a retaining direction,
in a second position of the valve plunger at least one of the fluid cylinders can be loaded at both sides with differing fluid flows, and
in a third position of the valve plunger at least one of the fluid cylinders can be loaded with a fluid counter to the retaining direction.

27. Instrument according to claim 26, wherein in the second position of the valve plunger a fluid flow is distributed unevenly to the two ports of at least one fluid cylinder.

28. Instrument according to claim 26, wherein:
the valve plunger is provided with a plurality of annular grooves and in the valve body in different switching positions defines different annular chambers,
the ratios of cross section of the different annular chambers in dependence upon a fluid pressure are mutually adapted in such a manner that in the second switching position only a fraction of a maximum actuating force may be generated by the at least one fluid cylinder.

29. Instrument according to claim 24, wherein at least two control valves are provided, each having at least two switching positions.

30. Instrument according to claim 29, wherein the at least two control valves are manually separately actuable.

31. Instrument according to claim 1, wherein on the tool part at least one coding element is provided for coding at least one of a nature and type of the tool part and on the handling part a decoding unit is provided for decoding at least one of a nature and type of the tool part.

32. Instrument according to claim 31, wherein:
the at least one coding element comprises at least one projection protruding from the tool part or at least one recess disposed in the tool part,
the decoding unit comprises an operating-mode switching member that corresponds to the at least one projection or the at least one recess,
the operating-mode switching member has at least a first and a second operating-mode position, and
the operating-mode switching member in accordance with the coding of the tool part occupies one of the at least two operating-mode positions.

33. Instrument according to claim 32, wherein the at least two operating-mode positions are associated with maximum actuating forces of the drive unit.

34. Instrument according to claim 32, wherein:
the operating-mode switching member is coupled to a control member which controls the drive unit, and
the operating-mode switching member in at least one operating-mode position directly or indirectly deactivates at least one switching position of the control member.

* * * * *